(12) United States Patent
Li et al.

(10) Patent No.: US 12,295,355 B2
(45) Date of Patent: May 13, 2025

(54) KIT FOR BREEDING A TGEV INFECTION RESISTANT PIG AND USE THEREOF

(71) Applicant: AGSINO GENSOURCES CO., LTD., Shenzhen (CN)

(72) Inventors: Kui Li, Shenzhen (CN); Yulian Mu, Shenzhen (CN); Lei Huang, Shenzhen (CN)

(73) Assignee: AGSINO GENSOURCES CO., LTD., Shenzhen (CN)

( * ) Notice: Subject to any disclaimer, the term of this patent is extended or adjusted under 35 U.S.C. 154(b) by 0 days.

(21) Appl. No.: 18/409,695

(22) Filed: Jan. 10, 2024

(65) Prior Publication Data

US 2024/0389561 A1 Nov. 28, 2024

(30) Foreign Application Priority Data

May 23, 2023 (CN) .......................... 202310584888.7

(51) Int. Cl.
*A01K 67/0275* (2024.01)
*C12N 9/22* (2006.01)
*C12N 15/11* (2006.01)
*C12N 15/85* (2006.01)

(52) U.S. Cl.
CPC ............ *A01K 67/0275* (2013.01); *C12N 9/22* (2013.01); *C12N 15/11* (2013.01); *C12N 15/8509* (2013.01); *A01K 2207/12* (2013.01); *A01K 2227/108* (2013.01); *A01K 2267/0337* (2013.01); *C12N 2015/8581* (2013.01); *C12N 2310/20* (2017.05)

(58) Field of Classification Search
CPC ............ A01K 67/0275; A01K 2207/12; A01K 2227/108; A01K 2267/0337; C12N 9/22; C12N 15/11; C12N 15/8509; C12N 2015/8581; C12N 2310/20
See application file for complete search history.

(56) References Cited

U.S. PATENT DOCUMENTS

2020/0236914 A1* 7/2020 Prather ............ C07K 14/70596
2023/0062272 A1* 3/2023 Li ...................... C12N 15/1138

FOREIGN PATENT DOCUMENTS

CN 113957069 A * 1/2022 .......... C12N 15/113

OTHER PUBLICATIONS

Ryu et al. Use of gene-editing technology to introduce targeted modifications in pigs. J Anim Sci Biotechnol. Jan. 29, 2018; 9:5; referenced as p. 1-10 (Year: 2018).*
Takara Bio. "How to design sgRNA sequences", blog post, Feb. 9, 2019; Retrieved from the Internet Jun. 21, 2024; https://www.takarabio.com/learning-centers/gene-function/gene-editing/gene-editing-tools-and-information/how-to-design-sgrna-sequences (Year: 2019).*
Chen et al. Production of porcine aminopeptidase N (pAPN) site-specific edited pigs. Anim Sci J. Jan. 8, 2019; 90(3):366-371. DOI: 10.1111/asj.13163 (Year: 2019).*
Tanihara et al. Current status of the application of gene editing in pigs. J Reprod Dev. Apr. 10, 2021; 67(3):177-187 (Year: 2021).*
Guo et al. Off-target effects in CRISPR/Cas9 gene editing. Front Bioeng Biotechnol. Mar. 9, 2023; 11:1143157; referenced as p. 1-11 . doi: 10.3389/fbioe.2023.1143157 (Year: 2023).*
First Office Action issued in Chinese Patent Application No. 202310584888.7; mailed Sep. 26, 2023; 12 pgs.

* cited by examiner

*Primary Examiner* — Titilayo Moloye
*Assistant Examiner* — Gillian C. Reglas
(74) *Attorney, Agent, or Firm* — HAUPTMAN HAM, LLP

(57) ABSTRACT

A kit for breeding a pig breed with resistance to the porcine transmissible gastroenteritis virus infection and application thereof. The systems includes a genetically edited protein, pAPN-sgRNA-1, pAPN-sgRNA-2, and a donor DNA. Effectively enzymatic cleavage can be made in two target sites of a pAPN gene by the gene editing protein. By replacing the fragment to be site-directed modified located between two target sites with donor DNA, a codon encoding tryptophan at position 737 in pAPN protein can be mutated to a codon encoding alanine, thereby achieving precise mutation of tryptophan to alanine at position 737 in a pAPN protein. The systems can avoid disruption or alteration of the normal expression of other amino acids in pAPN protein, therefore, the present invention maximally retains the physiological activity function of pAPN protein on the basis of resisting TGEV infection.

3 Claims, 5 Drawing Sheets

Specification includes a Sequence Listing.

```
                              SEQUENCE LISTING

Sequence total quantity: 21
SEQ ID NO: 1            moltype = DNA   length = 23
FEATURE                 Location/Qualifiers
source                  1..23
                        mol_type = other DNA
                        organism = synthetic construct
SEQUENCE: 1
ctagaaatac ctcaggaagc agg                                              23

SEQ ID NO: 2            moltype = DNA   length = 23
FEATURE                 Location/Qualifiers
source                  1..23
                        mol_type = other DNA
                        organism = synthetic construct
SEQUENCE: 2
cgagcgccca gaaaatctga tgg                                              23

SEQ ID NO: 3            moltype = DNA   length = 1000
FEATURE                 Location/Qualifiers
source                  1..1000
                        mol_type = other DNA
                        organism = synthetic construct
SEQUENCE: 3
cctttgagca cagtctggcc ttgtgcgagg cctttagcct ctggcctctt gctcctgtag      60
ccattagctc ttgctacatc tgcccaccca catcagaggc tccatgggtc tccagatgac     120
tcaggcatga gtctcttctt tgaagctatt tttagggctg catcctcggc atgtggaggt     180
tcccaagcta ggggttgaat cggagctgta gccgccagcc tacaccacag ccacagcaac     240
acgggatccg agccacatct gcgacctaca ccacagctca cagcaatgcc agatccttaa     300
cccactgagt ggggccaggg ttgaacccat gtcctcatgt ttcccagtca gattcgtttc     360
tgctgtgcca tgacgggaac tctggaactt cctctttgaa gctctttatg ttttgttctt     420
gttttttgtt tttgtttttc tagaaatacc tcaggaagca agtcgaaccc ctcttccaac     480
atttcgaaac tctcactaaa aacgccaccg agcgcccaga aaacttaatg gaccagtgag     540
tatgagctcg cttggtctgg agatcatggg tggtgcaggt agcctgacct gggggcccat     600
agcaagtcca gcagcatcct ctctggagct cccaactcct ggccggacca gggccacagt     660
cagggagagc gacccctccc aaccccactc ccggcccag gagtagggac tctgctctga      720
ggctctgtgt ggcctatgaa ccatctggcc tctttgggca aaggaccaaa ctgaacctct     780
gagggtccct cacccgcatg gtgaggttct aggtgttaaa gctggggctg gagcctgtgc     840
cagccctccc caggctgccc aagggcaaga agcaaagaag ggaacccaaa ggtggctggt     900
gggctatacc tgcagagtgc gggtctgcct ccctgttggg agttgtgtgt cagcagggga     960
gtcttggtca gcgtcaggtc caggcgtgct gacagagtgt                           1000

SEQ ID NO: 4            moltype = DNA   length = 1000
FEATURE                 Location/Qualifiers
source                  1..1000
                        mol_type = other DNA
                        organism = synthetic construct
SEQUENCE: 4
cctttgagca cagtctggcc ttgtgcgagg cctttagcct ctggcctctt gctcctgtag      60
ccattagctc ttgctacatc tgcccaccca catcagaggc tccatgggtc tccagatgac     120
tcaggcatga gtctcttctt tgaagctatt tttagggctg catcctcggc atgtggaggt     180
tcccaagcta ggggttgaat cggagctgta gccgccagcc tacaccacag ccacagcaac     240
acgggatccg agccacatct gcgacctaca ccacagctca cagcaatgcc agatccttaa     300
cccactgagt ggggccaggg ttgaacccat gtcctcatgt ttcccagtca gattcgtttc     360
tgctgtgcca tgacgggaac tctggaactt cctctttgaa gctctttatg ttttgttctt     420
gttttttgtt tttgtttttc tagaaatacc tcaggaagca agtcgaaccc ctcttccaac     480
atttcgaaac tctcactaaa aactggaccg cccgcccaga aaacttaatg gaccagtgag     540
tatgagctcg cttggtctgg agatcatggg tggtgcaggt agcctgacct gggggcccat     600
agcaagtcca gcagcatcct ctctggagct cccaactcct ggccggacca gggccacagt     660
cagggagagc gacccctccc aaccccactc ccggcccag gagtagggac tctgctctga      720
ggctctgtgt ggcctatgaa ccatctggcc tctttgggca aaggaccaaa ctgaacctct     780
gagggtccct cacccgcatg gtgaggttct aggtgttaaa gctggggctg gagcctgtgc     840
cagccctccc caggctgccc aagggcaaga agcaaagaag ggaacccaaa ggtggctggt     900
gggctatacc tgcagagtgc gggtctgcct ccctgttggg agttgtgtgt cagcagggga     960
gtcttggtca gcgtcaggtc caggcgtgct gacagagtgt                           1000

SEQ ID NO: 5            moltype = DNA   length = 25
FEATURE                 Location/Qualifiers
source                  1..25
                        mol_type = other DNA
                        organism = synthetic construct
SEQUENCE: 5
caccgctaga aatacctcag gaagc                                            25
```

```
SEQ ID NO: 6              moltype = DNA  length = 25
FEATURE                   Location/Qualifiers
source                    1..25
                          mol_type = other DNA
                          organism = synthetic construct
SEQUENCE: 6
aaacgcttcc tgaggtattt ctagc                                        25

SEQ ID NO: 7              moltype = DNA  length = 25
FEATURE                   Location/Qualifiers
source                    1..25
                          mol_type = other DNA
                          organism = synthetic construct
SEQUENCE: 7
caccgcgagc gcccagaaaa tctga                                        25

SEQ ID NO: 8              moltype = DNA  length = 25
FEATURE                   Location/Qualifiers
source                    1..25
                          mol_type = other DNA
                          organism = synthetic construct
SEQUENCE: 8
aaactcagat tttctgggcg ctcgc                                        25

SEQ ID NO: 9              moltype = DNA  length = 2919
FEATURE                   Location/Qualifiers
source                    1..2919
                          mol_type = other DNA
                          organism = synthetic construct
SEQUENCE: 9
atggccaagg gattctacat ttccaaggcc ctgggcatcc tgggcatcct cctcggcgtg    60
gcggccgtgg ccaccatcat cgctctgtct gtggtgtacg cccaggagaa gaacaagaat   120
gccgagcatg tcccccaggc cccacgtcg cccaccatca ccaccacagc cgccatcacc   180
ttggaccaga gcaagccgtg gaaccggtac cgcctaccca aacgctgtt gcctgattcc   240
tacaacgtga cgctgagacc ctacctcact cccaacgcgg atggcctgta catcttcaag   300
ggcaaaagca tcgtccgctt catctgccag gagcccaccg atgtcatcat catccatagc   360
aagaagctca actacaccac ccaggggcac atggtggtcc tgcggggcgt ggggggactcc   420
caggtcccag agatcgacag gactgagctg gtagagctca ctgagtacct ggtggtccac   480
ctcaagggct cgctgcagcc cggccacatg tacgagatgg agagtgaatt ccaggggggaa   540
cttgccgacg acctggcagg cttctaccgc agcgagtaca tggagggcaa cgtcaaaaag   600
gtgctggcca cgacacagat gcagtctaca gatgcccgga atccttccc atgctttgac   660
gagccagcca tgaaggccac gttcaacatc actctcatcc accctaacaa cctcacggcc   720
ctgtccaata tgccgcccaa aggttccagc accccacttg cagaagaccc caactggtct   780
gtcactgagt tcgaaaccac acctgtgatg tccacgtacc ttctggccta catcgtgagc   840
gagttccaga gcgtgaatga aacggcccaa aatgcgcgtc tgatccggat ctgggctcgg   900
cctaatgcaa ttgcagaggg ccatgcatg tatgccctga atgtgacagg tcccatccta   960
aacttctttg ccaatcatta taatacaccc tacccactcc caaatccga ccagattgcc  1020
ttgcccgact tcaatgccgg tgccatgag aactgggggc tgttgaccta ccgggagaac  1080
gcgctgctgt ttgaccccac gtcctcctcc atcagcaaca agagcgagt tgtcactgtg  1140
attgctcacg agctggccca ccagtggttt ggcaacctgg tgaccctggc ctggtggaat  1200
gacctgtggc tgaatgaggg cttgcctcc tatgtggagt acctgggtgc tgaccacgca  1260
gagcccacct ggaatctgaa agacctcatc gtgccaggcg acgtgtaccg agtgatggct  1320
gtggatgctc tggcttcctc ccaccccgctg accacccctg ctgaggaggt caacacacct  1380
gcccagatca gcgagatgtt tgactccata cctacagca agggagccct ggttatcagg  1440
atgctctcca acttcctgac tgaggacctg ttcaaggagg gcctggcgtc ctacttgcat  1500
gccttgcct atcagaacac cacctacctg gacctgtggg agcacctgca gaaggctgtg  1560
gatgctcaga cgtccatcag gctgccagac actgtgagag ccatcatgga tcgatggacc  1620
ctgcagatgg gcttccccgt catcaccgtg gacaccaaga caggaaacat ctcacagaag  1680
cacttcctcc tcgactccga atccaacgtc acccgctcct cagcgttcga ctacctctgg  1740
attgttccca tctcatctat taaaaatggt gtgatgcagg atcactactg gctgcgggat  1800
gtttcccaag cccagaatga tttgttcaaa accgcatcgg acgattgggt cttgctgaac  1860
atcaacgtga caggctattt ccaggtgaac tacgacgagg acaactggag gatgattcag  1920
catcagctgc agacaaacct gtcggtcatc cctgtcatca atcgggctca ggtcatctac  1980
gacagcttca acctgccac tgccacatg gtccctgtca ccctggctct ggacaacacc  2040
ctcttcctga acggagagaa agagtacatg cctggcagg ccgccctgag cagcctgagc  2100
tacttcagcc tcatgttcga ccgctccgag gtctatggcc ccatgaagaa ataccctcagg  2160
aagcaggtcg aaccctctt ccaacatttc gaaactctca ctaaaaactg gccgagcgc  2220
ccagaaaatc tgatggacca gtacagtgag attaatgcca tcagcactgc ctgctccaat  2280
ggattgcctc aatgtgagaa tctggccaag acccttttcg accagtggat gagcgaccca  2340
gaaaataacc cgatccaccc caacctgcgg tccaccatct actgcaatgc catagcccag  2400
ggcggccagg accagtggga ctttgcctgg gggcagttac aacaagccca gctggtaaat  2460
gaggccgaca aactccgctc agcgctggcc tgcagcaacg aggtctggct cctgaacagg  2520
tacctgggtt cacccctgaa cccggacctc attcggaagc aagacgccac ctccactatt  2580
aacagcattg ccagcaatgt catcgggcag cctctggcct gggattttgt ccagagcaac  2640
tggaagaagc tctttcagga ctatggcggt gttccttctc ccttcccaa cctcatccag  2700
ggtgtgaccc gaagattctc ctctgagttt gagctgcagc agctgagca gttcaagaag  2760
aacaacatgg atgtgggctt cggctccggc acccggggctc tggagcaagc cctggagaag  2820
accaaggcca acatcaagtg ggtgaaggag aacaaggagt ggtgtgttgaa ttggttcata  2880
```

```
gagcacagct acccatacga cgtcccagac tacgcttaa                          2919

SEQ ID NO: 10            moltype = DNA  length = 2919
FEATURE                  Location/Qualifiers
source                   1..2919
                         mol_type = other DNA
                         organism = synthetic construct
SEQUENCE: 10
atggccaagg gattctacat tccaaggcc ctgggcatcc tgggcatcct cctcggcgtg    60
gcggccgtgg ccaccatcat cgctctgtct gtggtgtacg cccaggagaa gaacaagaat    120
gccgagcatg tccccaggc ccccacgtcg cccaccatca ccaccacagc cgccatcacc    180
ttggaccaga gcaagccgtg gaaccggtac cgcctaccca aacgctgtt gcctgattcc    240
tacaacgtga cgctgagacc ctacctcact cccaacgcgg atggcctgta catcttcaag    300
ggcaaaagca tcgtccgctt catctgccag gagcccaccg atgtcatcat catccatagc    360
aagaagctca actacaccac ccaggggcac atggtggtcc tgcggggcgt ggggactcc    420
caggtcccag agatcgacag gactgagctg gtagagctca ctgagtacct ggtggtccac    480
ctcaagggct cgctgcagcc cggccacatg tacgagatgg agagtgaatt ccaggggaa    540
cttgccgacg acctggcagg cttctaccgc agcagtaca tggagggcaa cgtcaaaaag    600
gtgctggcca cgacacagat gcagtctaca gatgcccgga aatccttccc atgctttgac    660
gagccagcca tgaaggccac gttcaacatc actctcatcc accctaacaa cctcacggcc    720
ctgtccaata tgccgcccaa aggttccagc accccacttg cagaagaccc caactggtct    780
gtcactgagt tcgaaaccac acctgtgatg tccacgtacc ttctggccta catcgtgagc    840
gagttccaga gcgtgaatga aacgcccaa aatggcgtcc tgatccggat ctgggctcgg    900
cctaatgcaa ttgcagaggg ccatggcatg tatgccctga atgtgacagg tcccatccta    960
aacttctttg ccaatcatta taatacaccc tacccactcc caaatccga ccagattgcc    1020
ttgccgact tcaatgccgg tgccatggaa aactggggc tggtgccatca ccggagaac    1080
gcgctgctgt ttgacccaca gtcctcctcc atcagcaaca aagagcgagt tgtcactgtg    1140
attgctcacg agctggccca ccagtggttt ggcaacctgg tgaccctggc ctggtggaat    1200
gacctgtggc tgaatgaggg cttgccctcc tatgtggagt acctgggtgc tgaccacgca    1260
gagccacct ggaatctgaa agacctcatc gtgccaggcc acgtgtaccg agtgatggct    1320
gtggatgctc tggcttcctc ccaccccgctg accaccccctg ctgaggaggt caacacacct    1380
gcccagatca gcgagatgtt tgactccatc tcctacagca agggagcctc ggttatcagg    1440
atgctctcca acttcctgac tgaggacctg ttcaaggagg gcctggcgtc ctacttgcat    1500
gcctttgcct atcagaacac cacctacctg gacctgtggg agcacctgca gaaggctgtg    1560
gatgctcaga cgtccatcag gctgccagac actgtgagga ccatcatgga tcgatgacc    1620
ctgcagatgg gcttccccgt catcaccgtg gacaccaaga caggaaacat ctcacagaag    1680
cacttcctcc tcgactccga atccaacgtc accgctcct cagcgttcga ctacctctgg    1740
attgttccca tctcatctat taaaaatggt gtgatgcagg atcactactg gctgcgggat    1800
gtttcccaag cccagaatga tttgttcaaa accgcatcgg acgattgggt cttgctgaac    1860
atcaacgtga caggctattt ccaggtgaac tacgacgagg acaactggag gatgattcag    1920
catcagctgc agacaaacct gtcggtcatc cctgtcatca atcgggctca ggtcatctac    1980
gacagcttca acctggccac tgcccacatg gtccctgtca ccctggctct ggacaacacc    2040
ctcttcctga acggagagaa agagtacatg cccctggcag cgccctgga cagcctgagc    2100
tacttcagcc tcatgttcga ccgctccgag gtctatggcc ccatgaagaa atacctcagg    2160
aagcaggtcg aacccctctt ccaacatttc gaaactctca ctaaaaacgc caccgagcgc    2220
ccagaaaatc tgatggacca gtacagtgag attaatgcca tcagcactgc ctgctccaat    2280
ggattgcctc aatgtgagaa tctggccaga acccttttcg accagtggat gagcgaccca    2340
gaaaataacc cgatccaccc caacctgcgg tccaccatct actgcaatgc catagccaag    2400
ggcggccagg accagtggga cttttgcctgg gggcagttac aacaagccca gctggtaaat    2460
gaggccgaca aactccgctc agcgctggcc tgcagcaacg aggtctggct cctgaacagg    2520
tacctgggtt acaccctgaa cccggacctc attcggaagc aagacgccac ctccactctt    2580
aacagcattg ccagcaatgt catcgggcag cctctggcct gggattttgt ccagagcaac    2640
tggaagaagc tctttcagga ctatggcggt ggttccttct cctctccaa cctcatccag    2700
ggtgtgaccc gaagattctc ctctgagttt gagctgcagc agctggagca gttcaagaag    2760
aacaacatgg atgtgggctt cggctccggc acccgggctc tggagcaagc cctggagaag    2820
accaaggcca acatcaagtg ggtgaaggag aacaaggagg tggtgttgaa ttggttcata    2880
gagcacagct acccatacga cgtcccagac tacgcttaa                          2919

SEQ ID NO: 11            moltype = DNA  length = 2919
FEATURE                  Location/Qualifiers
source                   1..2919
                         mol_type = other DNA
                         organism = synthetic construct
SEQUENCE: 11
atggccaagg gattctacat tccaaggcc ctgggcatcc tgggcatcct cctcggcgtg    60
gcggccgtgg ccaccatcat cgctctgtct gtggtgtacg cccaggagaa gaacaagaat    120
gccgagcatg tccccaggc ccccacgtcg cccaccatca ccaccacagc cgccatcacc    180
ttggaccaga gcaagccgtg gaaccggtac cgcctaccca aacgctgtt gcctgattcc    240
tacaacgtga cgctgagacc ctacctcact cccaacgcgg atggcctgta catcttcaag    300
ggcaaaagca tcgtccgctt catctgccag gagcccaccg atgtcatcat catccatagc    360
aagaagctca actacaccac ccaggggcac atggtggtcc tgcggggcgt ggggactcc    420
caggtcccag agatcgacag gactgagctg gtagagctca ctgagtacct ggtggtccac    480
ctcaagggct cgctgcagcc cggccacatg tacgagatgg agagtgaatt ccaggggaa    540
cttgccgacg acctggcagg cttctaccgc agcagtaca tggagggcaa cgtcaaaaag    600
gtgctggcca cgacacagat gcagtctaca gatgcccgga aatccttccc atgctttgac    660
gagccagcca tgaaggccac gttcaacatc actctcatcc accctaacaa cctcacggcc    720
ctgtccaata tgccgcccaa aggttccagc accccacttg cagaagaccc caactggtct    780
gtcactgagt tcgaaaccac acctgtgatg tccacgtacc ttctggccta catcgtgagc    840
gagttccaga gcgtgaatga aacgcccaa aatggcgtcc tgatccggat ctgggctcgg    900
```

```
cctaatgcaa ttgcagaggg ccatggcatg tatgccctga atgtgacagg tcccatccta    960
aacttctttg ccaatcatta taatacaccc tacccactcc ccaaatccga ccagattgcc   1020
ttgcccgact tcaatgccgg tgccatggag aactgggggc tggtgaccta ccgggagaac   1080
gcgctgctgt ttgacccaca gtcctcctcc atcagcaaca aagagcgagt tgtcactgtg   1140
attgctcacg agctggccca ccagtggttt ggcaacctgg tgaccctggc ctggtggaat   1200
gacctgtggc tgaatgaggg cttttgcctc tatgtggagt acctgggtgc tgaccacgca   1260
gagcccacct ggaatctgaa agacctcatc gtgccaggcg acgtgtaccg agtgatggct   1320
gtggatgctc tggcttcctc ccacccgctg accaccctg ctgaggaggt caacacacct   1380
gcccagatca gcgagatgtt tgactccatc tcctacagca agggagcctc ggttatcagg   1440
atgctctcca acttcctgac tgaggacctg ttcaaggagg gcctggcgtc ctacttgcat   1500
gcctttgcct atcagaacac cacctacctg gacctgtggg agcacctgca gaaggctgtg   1560
gatgctcaga cgtccatcag gctgccagac actgtgagag ccatcatgga tcgatggacc   1620
ctgcagatgg gcttccccgt catcaccgtg gacaccaaga caggaaacat ctcacagaag   1680
cacttcctcc tcgactccga atccaacgtc acccgctcct cagcgttcga ctacctctgg   1740
attgttccca tctcatctat taaaaatggt gtgatgcagg atcactactg gctgcggat    1800
gtttcccaag cccagaatga tttgttcaaa accgcatcgg acgattgggt cttgctgaac   1860
atcaacgtga caggctattt ccaggtgaac tacgacgagg acaactggag gatgattcag   1920
catcagctgc agacaaacct gtcggtcatc cctgtcatca atcgggctca ggtcatctac   1980
gacagcttca acctgccac tgcccacatg gtccctgtca ccctggctct ggacaacacc   2040
ctcttcctga acggagagaa agagtacatg ccctggcagg ccgccctgag cagcctgagc   2100
tacttcagcc tcatgttcga ccgctccgag gtctatggcc ccatgaagaa ataccctcagg   2160
aagcaggtcg aacccctctt ccaacatttc gaaactctca ctaaaaactg gaccgcccgc   2220
ccagaaaatc tgatggacca gtacagtgag attaatgcca tcagcactgc ctgctccaat   2280
ggattgcctc aatgtgagaa tctgccaag acccttttcg accagtggat gagcgaccca   2340
gaaaataacc cgatccaccc caacctgcgg tccaccatct actgcaatgc catagcccag   2400
ggcggccagg accagtggga cttttgcctg gggcagttac aacaagccac gctggtaaat   2460
gaggccgaca aactccgctc agcgctggcc tgcagcaacg aggtctggct cctgaacagg   2520
tacctgggtt acaccctgaa cccggacctc attcggaagc aagacgccac ctccactatt   2580
aacagcattg ccagcaatgt catcgggcag cctctggcct gggattttgt ccagagcaac   2640
tggaagaagc tctttcagga ctatgcggt ggttccttct ccttctccaa cctccatccag   2700
ggtgtgaccc gaagattctc ctctgagttt gagctgcagc agctggagca gttcaagaag   2760
aacaacatgg atgtgggctt cggctccggc acccgggctc tggagcaagc cctggagaag   2820
accaaggcca acatcaagtg ggtgaaggag aacaaggagg tggtgttgaa ttggttcata   2880
gagcacagct acccatacga cgtcccagac tacgcttaa                         2919

SEQ ID NO: 12             moltype = DNA   length = 20
FEATURE                   Location/Qualifiers
source                    1..20
                          mol_type = other DNA
                          organism = synthetic construct
SEQUENCE: 12
caaggatttg tggaggagaa                                                20

SEQ ID NO: 13             moltype = DNA   length = 18
FEATURE                   Location/Qualifiers
source                    1..18
                          mol_type = other DNA
                          organism = synthetic construct
SEQUENCE: 13
gctgagcgga gtttgtcg                                                  18

SEQ ID NO: 14             moltype = DNA   length = 46
FEATURE                   Location/Qualifiers
source                    1..46
                          mol_type = other DNA
                          organism = synthetic construct
SEQUENCE: 14
tcgaacccct cttccaacat ttcgaaactc tcactaaaaa cgccac                   46

SEQ ID NO: 15             moltype = DNA   length = 46
FEATURE                   Location/Qualifiers
source                    1..46
                          mol_type = other DNA
                          organism = synthetic construct
SEQUENCE: 15
tcgaacccct cttccaacat ttcgaaactc tcactaaaaa ctggac                   46

SEQ ID NO: 16             moltype = DNA   length = 21
FEATURE                   Location/Qualifiers
source                    1..21
                          mol_type = other DNA
                          organism = synthetic construct
SEQUENCE: 16
gagggcctat ttcccatgat t                                              21

SEQ ID NO: 17             moltype = DNA   length = 44
FEATURE                   Location/Qualifiers
source                    1..44
                          mol_type = other DNA
```

```
                        organism = synthetic construct
SEQUENCE: 17
catttcgaaa ctctcactaa aaactggacc gagcgcccag aaaa                    44

SEQ ID NO: 18           moltype = DNA  length = 44
FEATURE                 Location/Qualifiers
source                  1..44
                        mol_type = other DNA
                        organism = synthetic construct
SEQUENCE: 18
catttcgaaa ctctcactaa aaacgccacc gagcgcccag aaaa                    44

SEQ ID NO: 19           moltype = DNA  length = 44
FEATURE                 Location/Qualifiers
source                  1..44
                        mol_type = other DNA
                        organism = synthetic construct
SEQUENCE: 19
catttcgaaa ctctcactaa aaactggacc gcccgcccag aaaa                    44

SEQ ID NO: 20           moltype = DNA  length = 42
FEATURE                 Location/Qualifiers
source                  1..42
                        mol_type = other DNA
                        organism = synthetic construct
SEQUENCE: 20
tttcgaaact ctcactaaaa actggaccga gcgcccagaa aa                      42

SEQ ID NO: 21           moltype = DNA  length = 42
FEATURE                 Location/Qualifiers
source                  1..42
                        mol_type = other DNA
                        organism = synthetic construct
SEQUENCE: 21
tttcgaaact ctcactaaaa acgccaccga gcgcccagaa aa                      42
```

KIT FOR BREEDING A TGEV INFECTION RESISTANT PIG AND USE THEREOF

RELATED APPLICATIONS

The present application claims priority from Chinese Application Number 202310584888.7, filed May 23, 2023, the disclosure of which is hereby incorporated by reference herein in its entirety.

INCORPORATION BY REFERENCE

The sequence listing provided in the file entitled PUS1232322.xml, which is an Extensible Markup Language (XML) file that was created on Dec. 28, 2023, and which comprises 30,533 bytes, is hereby incorporated by reference in its entirety.

TECHNICAL FIELD

The present invention relates to the field of biotechnology, in particular to a kit for breeding a TGEV infection resistance pig and use thereof.

BACKGROUND

Transmissible gastroenteritis (TGE) is a highly contagious disease, originally known as the transmissible gastroenteritis virus (TGEV), which mainly causes diarrhea, vomiting, dehydration, and death in pigs, with a mortality rate of up to 100% in newborn piglets. Therefore, TGE is considered as one of the important transmissible diseases that harm the pig feeding industry. Currently, there are still no effective control and treatment methods for TGE. Although vaccination can alleviate the spread of the epidemic to a certain extent, conventional TGE vaccines also have shortcomings. With the continuous development of biotechnology, the use of gene editing technology to breed a new pig breed with viral diarrhea resistance is an industrial demand for green and healthy pig farming.

The invasion of TGEV into host cells is achieved by binding the S protein of the virus to specific receptor protein molecules on the host cell membrane. In terms of TGEV itself, differences in pathogenicity are often caused by multiple factors, including differences in one or more amino acids of a single gene fragment or the synergistic effect of multiple gene fragments. Previous studies have found that pAPN protein is a key receptor for TGEV entry into cells, but there have been no reports on the key amino acid site(s) by which this protein functions. Therefore, we explore the key amino acid sites of pAPN that determine the pathogenicity of TGEV, and create a genetically edited pig with precise mutation at key amino acid sites using gene editing technology, in order to lay a material foundation for breeding a new pig breed with resistance to TGEV infection, which has important scientific and practical significance for the pig industry.

SUMMARY OF THE INVENTION

The technical problem to be solved by the present invention is how to breed a pig breed with resistance to TGEV infection.

In order to solve the above technical problem, the present invention first provides a kit.

The kit provided by the present invention comprises a genetically edited protein, pAPN-sgRNA-1, pAPN-sgRNA-2, and a donor DNA;

the pAPN-sgRNA-1 and pAPN-sgRNA-2 target two different target sequences of a pAPN gene, respectively, and a fragment between the two different target sequences is designated as a fragment to be site-directed modified (not comprising the target sequences of pAPN-sgRNA-1 and pAPN-sgRNA-2), which comprises a codon encoding tryptophan at position 737 in a pAPN protein; and the donor DNA contains a fragment with site-directed modification, which is obtained by mutating the codon encoding tryptophan at position 737 in a pAPN protein to a codon encoding alanine in the fragment to be site-directed modified.

In the kit above, the genetically edited protein can be specifically Cas9, Cas9n, Cpf1, or C2c2, preferably Cas9 protein.

In the kit above, the donor DNA sequentially comprises a forward homologous arm sequence (comprising the target sequence of pAPN-sgRNA-1), which is any DNA fragment (not comprising the first nucleotide in the fragment with site-directed modification) extending forwardly (relative to the porcine genome sequence) from the corresponding site of the first nucleotide in the fragment to be site-directed modified, the fragment with site-directed modification, and a reverse homologous arm sequence (comprising the target sequence of pAPN-sgRNA-2), which is any DNA fragment (not comprising the last nucleotide in the fragment with site-directed modification) extending reversely (relative to the porcine genome sequence) from the corresponding site of the last nucleotide in the fragment to be site-directed modified.

The forward and reverse homologous arm sequences have a length of 100-900 bp, preferably 400-500 bp.

The pAPN-sgRNA-1 and pAPN-sgRNA-2 both target two different sites of interest on pAPN gene, which are enzymatically cleaved by the genetically edited protein and then recombined using donor DNA. The codon encoding tryptophan at position 737 in a pAPN protein is precisely replaced without variations in the remaining amino acids, thereby replacing the codon encoding tryptophan at position 737 in a pAPN protein with the codon encoding alanine. Specifically, under the guidance of pAPN-sgRNA-1 and pAPN-sgRNA-2, the genetically edited protein enzymatically cleaves the target of interest and guides the donor DNA to replace the original homologous fragments in the cell, so that a codon encoding tryptophan (TGG) at position 737 in a pAPN protein can be mutated to a codon encoding alanine (GCC), thereby achieving precise mutation of tryptophan to alanine at position 737 in the pAPN protein. Based on the precise modification of the amino acid at position 737 in the pAPN protein on the basis of resisting TGEV infection while capable of avoiding disruption or alteration of the normal expression of other amino acids in the pAPN protein, the system provided by the present invention maximally retains the physiological activity function of the pAPN protein, and has advantages of wide applicability and high efficiency for gene editing and the like, which provides strong support for the preparation and breeding of new TGEV-resistant pig varieties with a single amino acid precise mutation in pAPN.

In a practical application, in order to prevent the donor DNA from being recognized and cleaved by the pAPN-sgRNA-1 and/or pAPN-sgRNA-2, synonymous mutations can be made on one or more bases on the target sequence of the pAPN-sgRNA-1 and/or the target sequence of the pAPN-sgRNA-2 in the donor DNA.

Further, the target sequence of pAPN-sgRNA-1 is set forth in SEQ ID No.1.

The target sequence of pAPN-sgRNA-2 is set forth in SEQ ID No.2.

The nucleotide sequence of the fragment with site-directed modification is as follows:

(SEQ ID NO. 14)
TCGAACCCCTCTTCCAACATTTCGAAACTCTCACTAAAAACGCCAC.

The nucleotide sequence of the fragment that requires site-directed modification is as follows:

(SEQ ID NO. 15)
TCGAACCCCTCTTCCAACATTTCGAAACTCTCACTAAAAACTGGAC.

Still Further, the donor DNA is double stranded DNA as set forth in SEQ ID No.3.

In order to solve the above technical problem, the present invention also provides a set of vectors.

The set of vectors provided by the present invention includes vectors expressing the kit above.

Further, the set of vectors consists of a vector for expressing the genetically edited protein above and the pAPN-sgRNA-1 above, a vector for expressing the genetically edited protein above and the pAPN-sgRNA-2 above, and a vector containing the donor DNA above.

Still Further, the vector for expressing the genetically edited protein above and the pAPN-sgRNA-1 above is obtained by connecting the annealed double stranded DNA fragments from the single stranded DNAs set forth in SEQ ID No.5 and SEQ ID No.6 into a genetically edited backbone vector;

the vector for expressing the genetically edited protein above and the pAPN-sgRNA-2 above is obtained by connecting the annealed double stranded DNA fragments from the single stranded DNAs set forth in SEQ ID No.7 and SEQ ID No.8 into a genetically edited backbone vector.

The genetically edited backbone vector includes an encoding sequence of a genetically edited protein and an sgRNA encoding sequence, specifically pX330, pX260, pX334, pX335, pX458, pX459, pX461, pX462, pX551 or pX552, preferably pX458, which has characteristics of wide universality, good versatility, and high product maturity, thus higher efficiency for enzymatic cleavage can be achieved by using pX458 as the backbone of the vector for gene editing.

The kit or vectors provided by the present invention can be used to achieve site-directed modification of a pAPN gene, for example, the kit or vectors above can be used to construct a cell line with site-directed modification of a pAPN gene. Since the site at position 737 is the most important amino acid site that affects the activity of a TGEV receptor, its point mutation can block the binding of pAPN and TGEV, so as to resist the infection of TGEV, thereby greatly enhancing the body's resistance to TGEV, and constructing a pig with transmissible gastroenteritis resistance, in order to effectively solve the technical problems of breeding a pig breed with resistance to TGEV infection.

In order to solve the technical problems above, the present invention also provides a new use of a substance that mutates tryptophan to alanine at position 737 in a pAPN protein.

The present invention provides application of a substance that mutates tryptophan to alanine at position 737 in a pAPN protein in any of the following 1)-4):

1) preparing a product for prevention and/or treatment of transmissible gastroenteritis in pigs;
2) constructing a cell line with site-directed modification of a pAPN gene;
3) constructing a pig model with transmissible gastroenteritis resistance; and
4) breeding a pig breed with resistance to the porcine transmissible gastroenteritis virus infection.

The substance that mutates tryptophan to alanine at position 737 in a pAPN protein may be the kit or vectors above.

In order to solve the above technical problem, the present invention finally provides any of the following A1)-A3) methods:

A1) a method for constructing a cell line with site-directed modification of a pAPN gene, which comprises the steps of introducing the kit above or the set of vectors above into pig derived cells to obtain the cell line with site-directed modification of a pAPN gene;

A2) a method for breeding a pig breed with resistance to the porcine transmissible gastroenteritis virus infection, which comprises the steps of transplanting the cell line in A1) into enucleated oocytes to obtain recombinant cloned embryos, followed by transplantation into a maternal body for pregnancy to obtain a genetically edited pig with pAPN protein mutation that is the pig breed with resistance to the porcine transmissible gastroenteritis virus infection; and A3) a method for breeding a pig breed with resistance to the porcine transmissible gastroenteritis virus infection, which comprises the steps of microinjecting the kit above or the set of vectors above into the zygotic embryos in a pig to obtain a pAPN gene-modified embryo, followed by transplantation into a maternal body for pregnancy to obtain a genetically edited pig with pAPN protein mutation that is the pig breed with resistance to the porcine transmissible gastroenteritis virus infection.

In the method described in A1) above, the method for introducing may be electroporation or liposome transfection. The introduction further includes steps of screening and identification. A monoclonal cell may be screened by flow cytometric sorting in the method for screening. The method of identification may be sequencing identification, specifically, DNA from the monoclonal cell may be extracted, followed by PCR amplification using primers set forth in SEQ ID No. 12 and SEQ ID No.13 to obtain the amplified products, which are then sequenced to confirm whether the cell with precise modification.

In the methods of A2) and A3) above, a step of identification after birth is further comprised for the genetically edited pig. The method of identification may be sequencing identification, specifically, DNA from the genetically edited pig may be extracted, followed by PCR amplification using primers set forth in SEQ ID No. 12 and SEQ ID No.13 to obtain the amplified products, which are then sequenced to confirm precise modification.

The cell line with site-directed modification of a pAPN gene constructed according to the above method also belongs to the protection scope of the present invention.

In any of the above methods or applications or cells, the site-directed modification of a pAPN gene refers to the mutation of the codon (TGG) encoding tryptophan at position 737 in the pAPN protein to the codon (GCC) encoding alanine.

Compared with the prior art, the beneficial effects of the present invention are as follows: 1. the method for preparing a cell with site-directed modification of a pAPN gene using the kit of the present invention has advantages of simple operation and low cost with accurate modification of the amino acid at position 737 in pAPN in the prepared cell. 2. The method for preparing a genetically edited pig obtained by using the cell with site-directed modification of a pAPN gene has advantages of convenient operation and wide universality, and the prepared pig with precise gene editing not only have good TGEV resistance while retaining the physiological activity function of pAPN protein.

The kit provided by the present invention for breeding a pig breed with resistance to TGEV infection includes a genetically edited protein, pAPN-sgRNA-1, pAPN-sgRNA-2, and a donor DNA. Effectively enzymatic cleavage can be made in two target sites of a pAPN gene by the gene editing protein. By replacing the fragment to be site-directed modified located between two target sites with donor DNA, a codon encoding tryptophan (TGG) at position 737 in pAPN protein can be mutated to a codon encoding alanine (GCC), thereby achieving precise mutation of tryptophan to alanine at position 737 in pAPN protein. The method for site-directed modification of a pAPN gene based on the kit of the present invention may achieve precise modification of the amino acid at position 737 in pAPN protein while capable of avoiding disruption or alteration of the normal expression of other amino acids in pAPN protein, therefore, the present invention maximally retains the physiological activity function of pAPN protein on the basis of resisting TGEV infection, and has advantages of wide applicability and high efficiency for gene editing and the like.

BRIEF DESCRIPTION OF DRAWINGS

FIG. 4 is a graph of the results of fluorescence quantitative PCR (qRT-PCR) for detection of the copy number of TGEV RNA in overexpressed porcine ileal epithelial cells infected with TGEV, in which the amino acid at position 737 in pAPN protein is precisely modified, as provided in Example 2 of the present invention.

FIG. 5 is a graph of the results of Western Blot for detection of TGEV protein in overexpressed porcine ileal epithelial cells infected with TGEV, in which amino acids at position 737 in pAPN protein are precisely modified, as provided in Example 2 of the present invention.

FIG. 8 is a graph of the results of qPCR for detection of the copy number of TGEV RNA in porcine ileal epithelial cells infected with TGEV, in which the amino acid at position 739 in pAPN protein is precisely modified, as provided in Example 3 of the present invention.

FIG. 9 is a graph of the results of Western Blot for detection of TGEV protein in overexpressed porcine ileal epithelial cells infected with TGEV, in which amino acids at position 739 in pAPN protein are precisely modified, as provided in Example 3 of the present invention.

DETAILED DESCRIPTION

The present invention is further described in detail below in conjunction with the detailed description. The Examples provided are only for the purpose of elucidating the present invention, and are not intended to limit its scope. The Examples provided below may serve as a guide for persons of ordinary skill in the art to further improve and do not limit the present invention in any way.

The experimental methods in Examples below are conventional methods unless otherwise specified, and carried out according to the techniques or conditions described in the literature in art or in accordance with the product instruction. The materials, reagents and the like used in Examples below can be obtained commercially unless otherwise specified.

The main reagents involved in the Examples below and their sources were as follows: the collagenase type IV used for isolating porcine fetal fibroblasts was a product from Sigma. DMEM, FBS, PS, NEAA, Glutamine, and Trypase used for cell culture were all products from Gibco. The DNA extraction kit for cells and ear tissues was a product from Tiangen Biotech Co., Ltd. The KOD FX PCR enzyme used for PCR was a product from TOYOBO.

The primer sequences involved in the Examples below were synthesized by Beijing Tsingke Biotech Co., Ltd.

The main instruments involved in the Examples below were as follows: CO2 incubator (Thermo Scientific, 3111), clean bench (AIRTECH, SW-CJ-IFD), inverted fluorescence microscope (ZEISS, observerA1), PCR instrument (BIO-RID, C1000 Touch), gel imaging system (BIO-RID, Universal Hood II), micromanipulation system (Eppendorf, Celltramvario), flow cytometric sorter (BD, Aria III).

The amino acid sequence of the pAPN protein in the Examples below had GenBank No. NP_999442.1 in NCBI.

The amino acid sequence of Cas9 protein in the Examples below had GenBank No. ANW61896.1 in NCBI.

Porcine ileal epithelial cells with pAPN gene knockout (Immortal Pig Intestinal-2I Knock Out, IPI-2I-KO) in the Examples below could be found in the reference of "Xu Changjiang, Wang Xiaopeng, XuKui et al. Establishment of a pAPN gene knockout IPI-2I cell lines Mediated by CRISPR/Cas9 System [J]. China Animal Husbandry and Veterinary Medicine, 2021, 48 (7): 2282-2290. DOI: 10.16431/j.cnki. 1671-7236.2021.07.002.".

Example 1. Design of a System for Site-Directed Modification in pAPN Gene and Construction of Expression Vector Thereof I. Design of a System for Site-Directed Modification in pAPN Gene 1. Design of System 1 for Site-Directed Modification in pAPN Gene System 1 for site-directed modification in pAPN gene in the present invention comprised Cas9 protein, pAPN-sgRNA-1, pAPN-sgRNA-2, and donor DNA1 (dsODN sequence 1):

The target sequence of pAPN-sgRNA-1 was set forth in SEQ ID No.1.

The target sequence of pAPN-sgRNA-2 was set forth in SEQ ID No.2.

The donor DNA1 (dsODN sequence 1) was a double stranded DNA molecule set forth in SEQ ID No.3.

Figure 1:
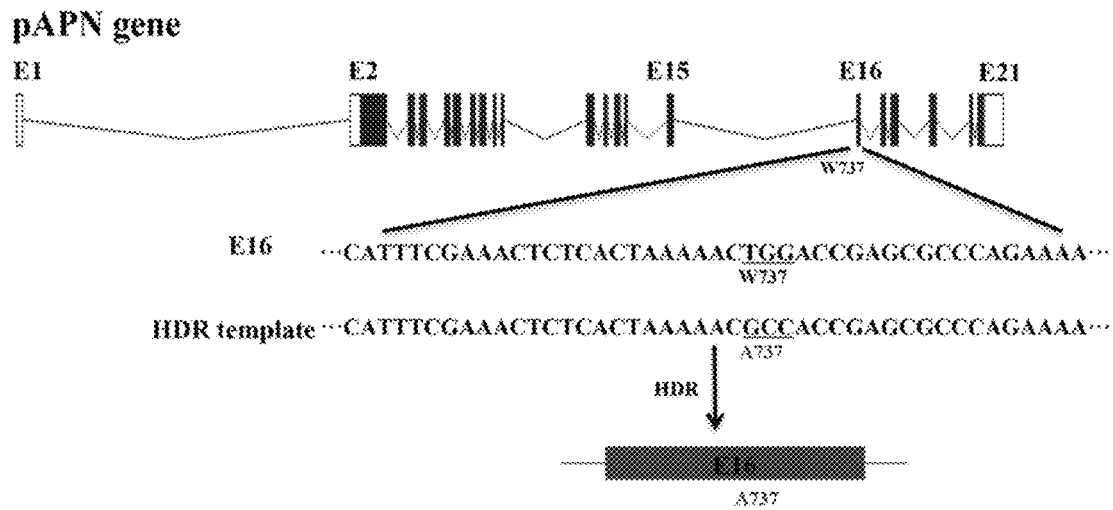
FIG. 1 is a pattern diagram of the precise mutation of W737 single amino acid in pig pAPN protein, as provided in Example 1 of the present invention. The nucleotide sequence of E16 is shown in SEQ ID NO.17, and the nucleotide sequence of HDR template is shown in SEQ ID NO. 18.

The codon encoding the amino acid at position 737 in a pAPN protein in the pig genome could be replaced with GCC from TGG by System 1 for site-directed modification in a pAPN gene in the present invention, so as to alter the amino acid at position 737 in the pAPN protein from tryptophan to alanine, and the specific mutation pattern was shown in FIG. 1.

2. Design of System 2 for Site-Directed Modification in a pAPN Gene

System 2 for site-directed modification in a pAPN gene in the present invention comprised Cas9 protein, pAPN-sgRNA-1, pAPN-sgRNA-2, and donor DNA2 (dsODN sequence 2):

The target sequence of pAPN-sgRNA-1 was set forth in SEQ ID No.1.

The target sequence of pAPN-sgRNA-2 was set forth in SEQ ID No.2.

The donor DNA2 (dsODN sequence 2) was a double stranded DNA molecule set forth in SEQ ID No.4.

Figure 2:
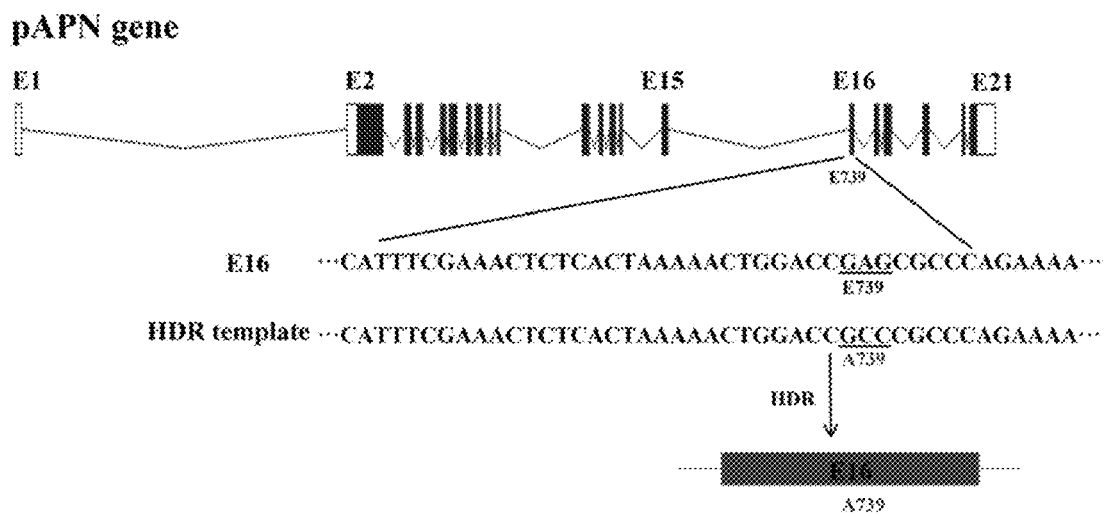
FIG. 2 is a pattern diagram of the precise mutation of E739 single amino acid in pig pAPN gene, as provided in Example 1 of the present invention. The nucleotide sequence of E16 is shown in SEQ ID NO. 17, and the nucleotide sequence of HDR template is shown in SEQ ID NO. 19.

The codon encoding the amino acid at position 739 in pAPN protein in the pig genome could be replaced with GCC from GAG by System 2 for site-directed modification in pAPN gene in the present invention, so as to alter the amino acid at position 739 in pAPN protein from glutamic acid to alanine, and the specific mutation pattern was shown in FIG. 2.

II. Construction of an Expression Vector for a System for Site-Directed Modification in a pAPN Gene 1. Construction of Recombinant Vectors pX458-pAPN-sgRNA-1 and pX458-pAPN-sgRNA-2

1) Synthesis of complementary paired oligonucleotide sequences as follows for pAPN-sgRNA-1 and pAPN-sgRNA-2 sequences:

pAPN-sgRNA-1-F:
(SEQ ID No. 5)
caccgCTAGAAATACCTCAGGAAGC;

pAPN-sgRNA-1-R:
(SEQ ID No. 6)
aaacGCTTCCTGAGGTATTTCTAGc;

-continued
pAPN-sgRNA-2-F:
(SEQ ID No. 7)
caccgCGAGCGCCCAGAAAATCTGA;

pAPN -sgRNA-2-R:
(SEQ ID NO. 8)
aaacTCAGATTTTCTGGGCGCTCGc.

2) The complementary oligonucleotides corresponding to pAPN-sgRNA-1 and pAPN-sgRNA-2 in step 1) were treated at 98° C. for 10 min, respectively, and then naturally cooled to the room temperature for annealing to obtain annealed double stranded fragments.

3) The PX458 backbone vector containing Cas9 encoding gene sequence (Addgene, #48138) was cleaved with the restrictive endonuclease Bbs I at 37° C. for 2 h, followed by recovery of the backbone of the linearized vector by gel cutting.

4) The annealed double-stranded fragments obtained in step 2) were connected with the backbone of the lincarized vector obtained in step 3) at 16° C. for 1 h, cooled in ice bath for 30 min, followed by heat shock for 45 s, and then transformed into Top10 or DH5a competent cells, which were coated and grown on LB plates containing ampicillin, and single colonies were picked on the next day for culturing and sequencing using primer GAGGGCCTATTTCCCAT-GATT (SEQ ID No.16).

5) After culturing the correctly sequenced single colonies, plasmids were extracted and named recombinant plasmids pX458-pAPN-sgRNA-1 and pX458-pAPN-sgRNA-2, respectively, and then frozen at −20° C. for subsequent cell transfection. The plasmid extraction was carried out using the EndoFree Plasmid Maxi Kit (CoWin Biotech, CW2104M).

The recombinant plasmid pX458-pAPN-sgRNA-1 was obtained by connecting the annealed double stranded DNA fragments set forth in SEQ ID No.5 and SEQ ID No.6 into the restriction endonuclease Bbs I site of the PX458 backbone vector.

The recombinant plasmid pX458-pAPN-sgRNA-2 was obtained by connecting the annealed double stranded DNA fragments set forth SEQ ID No.7 and SEQ ID No.8 to the restriction endonuclease Bbs I site of the PX458 backbone vector.

2. Construction of Donor Vector

1) Construction of Donor-737 Vector

The dsODN sequence 1 was connected into between the BamHI and Mlul restriction endonuclease sites in the PUC57 vector (GenScript Biotech Corporation, SD1176) to obtain the recombinant vector was obtained for sequencing validation. After culturing the correctly sequenced single colony, the plasmid was extracted and named Donor-737 for subsequent cell transfection. The plasmid extraction was carried out using the EndoFree Plasmid Maxi Kit (CoWin Biotech, CW2104M).

2) Construction of Donor-739 Vector

The dsODN sequence 2 was connected into between the BamHI and Mlul restriction endonuclease sites in the PUC57 vector (GenScript Biotech Corporation, SD1176) to obtain the recombinant vector was obtained for sequencing validation. After culturing the correctly sequenced single colony, the plasmid was extracted and named Donor-739 for subsequent cell transfection. The plasmid extraction was carried out using the EndoFree Plasmid Maxi Kit (CoWin Biotech, CW2104M).

Example 2 Establishment and Functional Verification of the Overexpressed Porcine Ileal Epithelial Cells with Precise Modification of the Amino Acid at Position 737 in a pAPN Gene I. Establishment of the Overexpressed Porcine Ileal Epithelial Cells with Precise Modification of the Amino Acid at Position 737 in a pAPN Gene 1. The CDS sequence of wild-type pAPN gene (SEQ ID No.9) was connected into a PLVX vector (Qincheng Biotechnology Co., Ltd., QCP0424) to obtain a PLVX-WT recombinant vector.

The CDS sequence of a pAPN gene (SEQ ID No.10) with precise modification of the amino acid at position 737 was connected into a PLVX vector (Qincheng Biotechnology Co., Ltd., QCP0424) to obtain a PLVX-737 recombinant vector.

2. On the day before electrotransfection, porcine ileal epithelial cells with pAPN gene knockout (Immortal Pig Intestinal-2I Knock Out, IPI-2I-KO) were recovered into 10 cm dishes, and the cell transfection could be performed until to about 80% confluence of cells.

3. PLVX-WT recombinant vector, PLVX-737 recombinant vector, and PLVX vector were electrotransfected into IPI-2I-KO cells to obtain successfully overexpressed cells with precise modification, named IPI-2I-WTOE, IPI-2I-737OE and IPI-2I-Vector respectively, for use as donor cells in subsequent TGEV infection.

II. Functional Verification

IPI-2I-WTOE, IPI-2I-737OE and IPI-2I-Vector cells obtained in above step I were tested for TGEV infection with specific steps of:

1. IPI-2I-WTOE, IPI-2I-737OE and IPI-2I-Vector cells were inoculated with TGEV virus strains (MOI=1), respectively.

2. Cells were collected at 12 h after infection, followed by extraction of cell proteins for detection of the expression of pAPN by Western blot. Meanwhile, IPI-2I-KO cells without virus inoculation were used as the Mock group.

Figure 3:
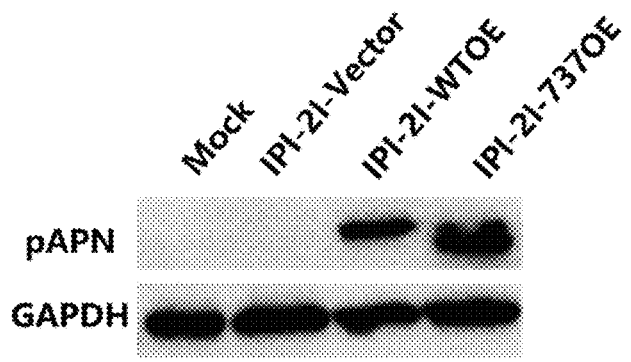
FIG. 3 is an expression graph showing overexpressed pAPN proteins in porcine ileal epithelial cells with precise modification of an amino acid at position 737 in pAPN protein, as provided in Example 2 of the present invention.

The results of pAPN protein detection were shown in FIG. 3, indicating that PAPNs were normally expressed in both the IPI-2I-WTOE and IPI-2I-737OE groups after virus inoculation.

3. Cells were collected at 12 h after infection, and washed 4-5 times with PBS, followed by extraction of RNA from cells for detection of the copy number of TGEV virus in cells by qRT-PCR. Meanwhile, IPI-2I-KO cells without virus inoculation were used as the Mock group.

Figures 4, 5:
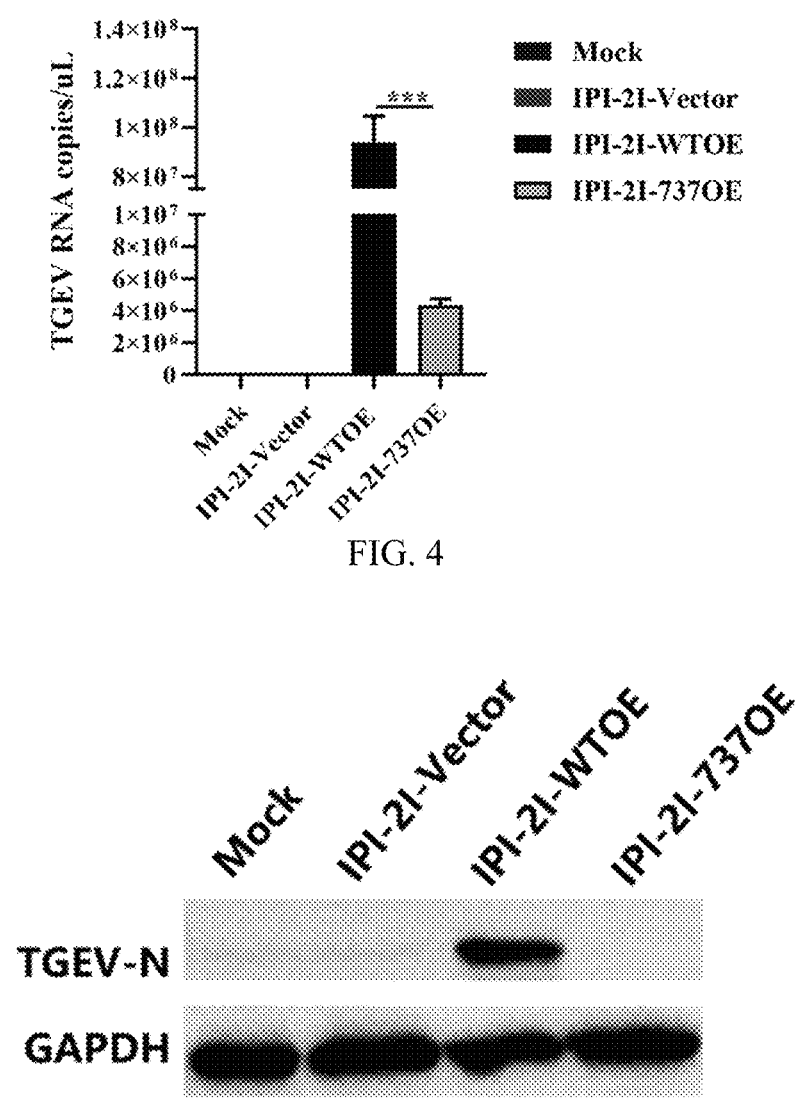

The qRT-PCR results were shown in FIG. 4, indicating that the copy number of TGEV genomic RNA in IPI-2I-737OE cells was significantly reduced (*** $P<0.001$), compared with IPI-2I-WTOE cells.

4. Cells were collected at 12 h after infection, followed by extraction of cell proteins for detection of the expression of TGEV virus by Western Blot. Meanwhile, IPI-2I-KO cells without virus inoculation were used as the Mock group.

The infection amount of TGEV virus was shown in FIG. 5, indicating that the amount of TGEV infection in cells of the IPI-2I-737OE group was significantly reduced, compared with cells of IPI-2I-WTOE group.

5. Cells were collected at 12 h after infection, followed by detection of TGEV infection in cells by IFA. Meanwhile, IPI-2I-KO cells without virus inoculation were used as the Mock group.

Figure 6:
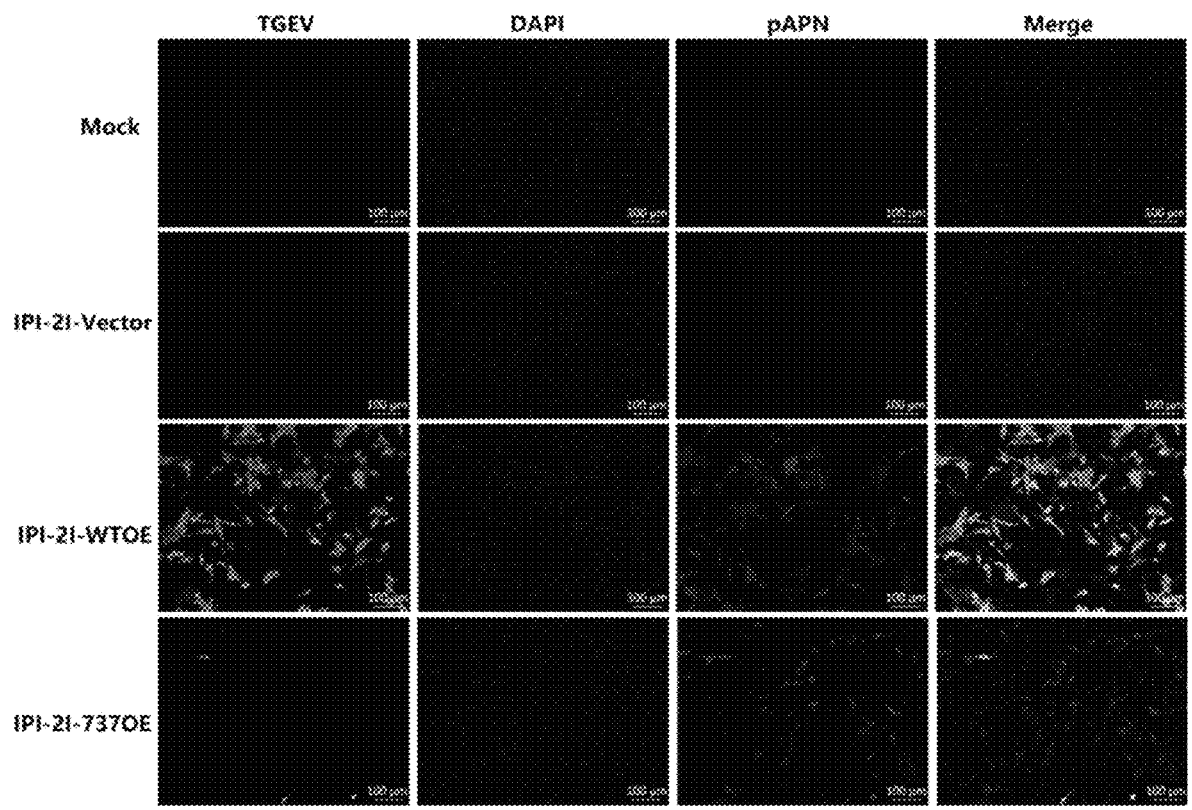
FIG. 6 is a graph of the results of indirect immunofluorescence assay (IFA) for detection of pAPN and TGEV expressions in overexpressed porcine ileal epithelial cells infected with TGEV, in which the amino acids at position 737 in pAPN protein is precisely modified, as provided in Example 2 of the present invention.

The IFA detection results were set forth in FIG. 6, indicating that IPI-2I-WT cells were infected with a large number of TGEVs after virus inoculation; and the amount of TGEV infection in IPI-2I-737OE cells was significantly reduced compared with IPI-2I-WT cells.

In summary, the above results showed that the overexpressed porcine ileal epithelial cells with precise modification of amino acids at position 737 in a pAPN gene could effectively resist TGEV infection, indicating that the position 737 in the pAPN gene was a key site for TGEV infection, and the precise modification of the amino acid at position 737 in pAPN gene could effectively resist TGEV infection.

Example 3. Establishment and Functional Verification of the Monoclone from Porcine Ileal Epithelial Cells with Precise Modification of the Amino Acid at Position 739 in a pAPN Gene 1. The CDS sequence of wild-type pAPN gene (SEQ ID No.9) was connected into a PLVX vector to obtain a PLVX-WT recombinant vector.

The CDS sequence of a pAPN gene (SEQ ID No.11) with precise modification of the amino acid at position 739 was connected into a PLVX vector to obtain a PLVX-739 recombinant vector.

2. On the day before electrotransfection, porcine ileal epithelial cells with pAPN gene knockout (Immortal Pig Intestinal-2I Knock Out, IPI-2I-KO) were recovered into 10 cm dishes, and the cell transfection could be performed until to about 80% confluence of cells.

3. PLVX-WT recombinant vector, PLVX-739 recombinant vector, and PLVX vector were electrotransfected into IPI-2I-KO cells to obtain successfully overexpressed cells with precise modification, named IPI-2I-WTOE, IPI-2I-739OE and IPI-2I-Vector respectively, for use as donor cells in subsequent TGEV infection.

II. Functional Verification

IPI-2I-WTOE, IPI-2I-739OE and IPI-2I-Vector cells obtained in above step I were tested for TGEV infection with the following specific steps 1. IPI-2I-WTOE, IPI-2I-739OE and IPI-2I-Vector cells were inoculated with TGEV virus strains (MOI=1), respectively.

2. Cells were collected at 12 h after infection, followed by extraction of cell proteins for detection of the expression of pAPN by Western Blot. Meanwhile, IPI-2I-KO cells without virus inoculation were used as the Mock group.

Figure 7:
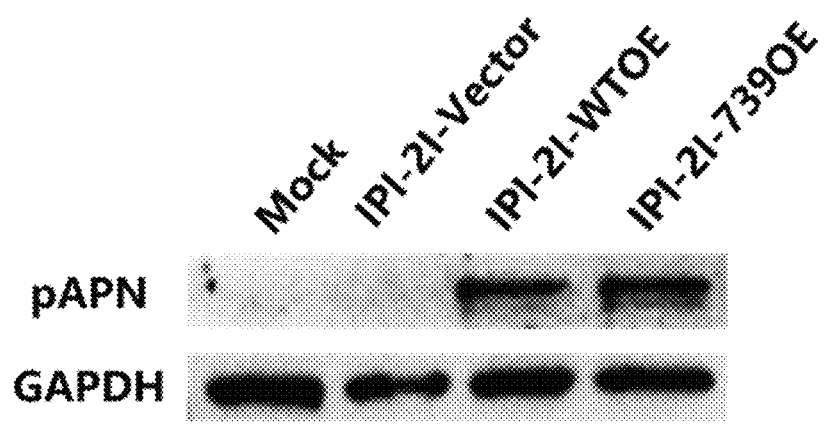
FIG. 7 is an expression graph showing overexpressed pAPN proteins in porcine ileal epithelial cells with precise modification of an amino acid at position 739 in pAPN protein, as provided in Example 3 of the present invention.

The results of pAPN protein detection were shown in FIG. 7, indicating that PAPNs were normally expressed in both the IPI-2I-WTOE and IPI-2I-739OE groups after virus inoculation.

3. Cells were collected at 12 h after infection, and washed 4-5 times with PBS, followed by extraction of RNA from cells for detection of the copy number of TGEV virus in cells by qRT-PCR. Meanwhile, IPI-2I-KO cells without virus inoculation were used as the Mock group.

Figures 8, 9:
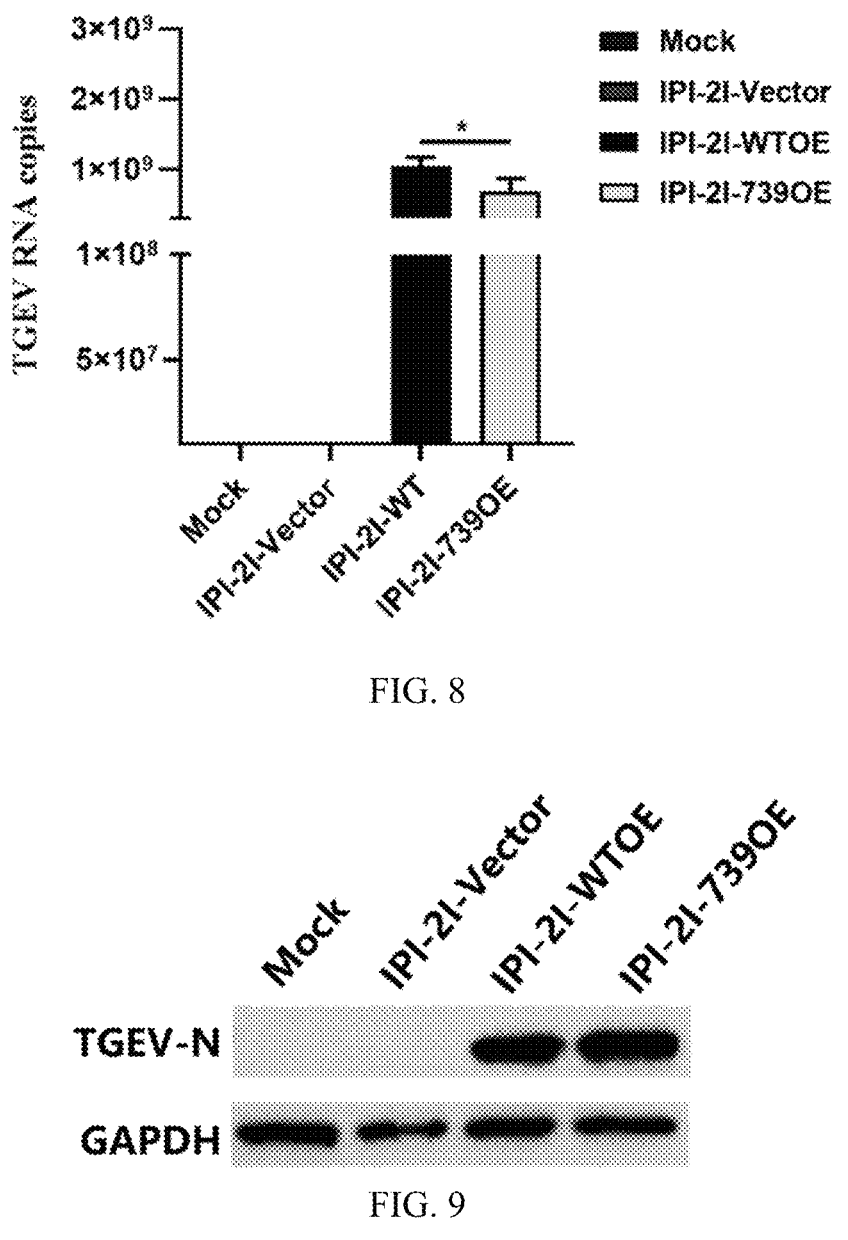

The qRT-PCR results were shown in FIG. 8, indicating that the copy number of TGEV genomic RNA in IPI-2I-7390E cells was significantly reduced (* $P<0.05$), compared with IPI-2I-WTOE cells.

4. Cells were collected at 12 h after infection, followed by extraction of cell proteins for detection of the expression of TGEV virus by Western Blot. Meanwhile, IPI-2I-KO cells without virus inoculation were used as the Mock group.

The infection amount of TGEV virus was shown in FIG. 9, indicating that there was no significant change in the amount of TGEV infection in cells of the IPI-2I-7390E group, compared with cells of IPI-2I-WTOE group.

5. Cells were collected at 12 h after infection, followed by detection of TGEV infection in cells by IFA. Meanwhile, IPI-2I-KO cells without virus inoculation were used as the Mock group.

Figure 10:
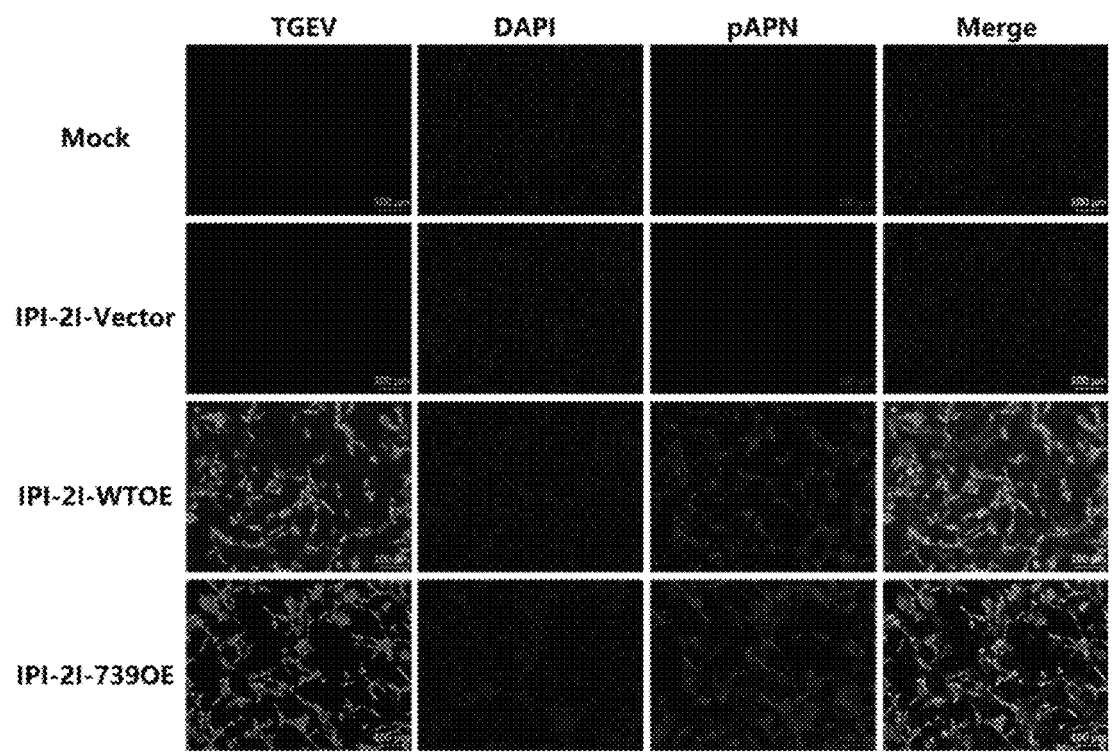
FIG. 10 is a graph of the results of IFA for detection of pAPN and TGEV expressions in overexpressed porcine ileal epithelial cells infected with TGEV, in which the amino acids at position 739 in pAPN protein is precisely modified, as provided in Example 3 of the present invention.

The IFA detection results were shown in FIG. 10, indicating that there was no significant change in the amount of TGEV infection in cells of the IPI-2I-7390E group, compared with cells of IPI-2I-WT group.

In summary, the above results showed that the overexpressed porcine ileal epithelial cells with precise modification of amino acids at position 739 in the pAPN gene could not effectively resist TGEV infection, indicating that the position 739 in the pAPN gene was not a key site for TGEV infection, and the precise modification of the amino acid at position 739 in the pAPN gene could not effectively resist TGEV infection.

Example 4. Establishment of the Monoclone from Porcine Fibroblasts with Precise Modification of the Amino Acid at Position 737 in a pAPN Gene I. Preparation of Porcine Fetal Fibroblasts The head, tail, limbs, viscera, and bones from a pig embryo at 35 days old were removed, and the blood was cleaned. The fetus was continuously cut using an elbow ophthalmic scissor for 30 min to ensure sufficient fragmentation, and then the fetal tissue fragments were pipetted into a 15 mL centrifuge tube using the head-cut blue tip, into which 5 mL of complete culture medium were added, followed by natural settlement for a few minutes to remove the supernatant, and a few drops of fetal bovine serum were added to the lower tissue block, which was sucked out using a 15 cm curved glass Pasteur tube bent at 1 cm from the tip, and placed into two T75 culture bottles with the bottom facing upwards, followed by addition of 15 mL of complete culture medium to the opposite side. The culture bottles were carefully turned over after 6-8 h, so that the tissue block was immersed in the culture medium with refreshment every two days to obtain cells, which were frozen and stored for future use until filling the T75 culture bottles. In this process, pigs were fed in the base pig farm of the Beijing Institute of Animal Science of CAAS.

II. Cell Transfection

The primary porcine fetal fibroblasts were recovered into a 10 cm plate at the day before transfection, and the cell transfection could be performed until to about 80% confluence of cells. 5 μg pX458-pAPN-sgRNA-1 plasmids prepared in Example 1, 5 μg pX458-pAPN-sgRNA-2 plasmids prepared in Example 1 and 5 μg Donor-737 plasmids prepared in Example 1 were co-transfected into porcine fetal fibroblasts with steps following strictly to the instructions of the Basic Primary Fibroblasts Nucleofector Kit (Lonza), and then the electrotransfected cells were transferred to a 6-well plate for culture.

III. Flow Cytometric Sorting and Passage of Monoclonal Cells

Cells were digested and collected into a tube for flow cytometry at 48 h after electroporation. Individual GFP positive cells were sorted using a flow cytometric sorter and cultured in a 96-well plate with refreshment of the culture medium every 3 days. Cells were passaged to a 48 well plate for culture until filling the 96-well plate, and then a portion of cells were taken for genome extraction and genotype identification until filling the 48 well plate.

IV. Identification of Monoclonal Cells

The picked monoclonal cells were identified with specific steps of: the extracted cell genomic DNA as a template, using pAPN-TY-F2 and pAPN-TY-R2 for PCR amplification to obtain PCR products with a size of 1443 bp.

```
pAPN-TY-F2:
                                    (SEQ ID No. 12)
5'-CAAGGATTTGTGGAGGAGAA-3';

pAPN-TY-R2:
                                    (SEQ ID NO. 13)
5'-GCTGAGCGGAGTTTGTCG-3'.
```

The amplification condition for PCR was as follows: 94° C. for 5 min; 94° C. for 30 s, 62.6° C. for 30 s, 68° C. for 1 min 40 s, 34 cycles; 72° C. for 5 min. PCR products were sequenced by Beijing TianyiHuiyuan Company. Based on the results of sequencing, porcine fibroblasts with precise modification of the amino acid at position 737 in pAPN protein were screened as donor cells for nuclear transplantation.

Figure 11:
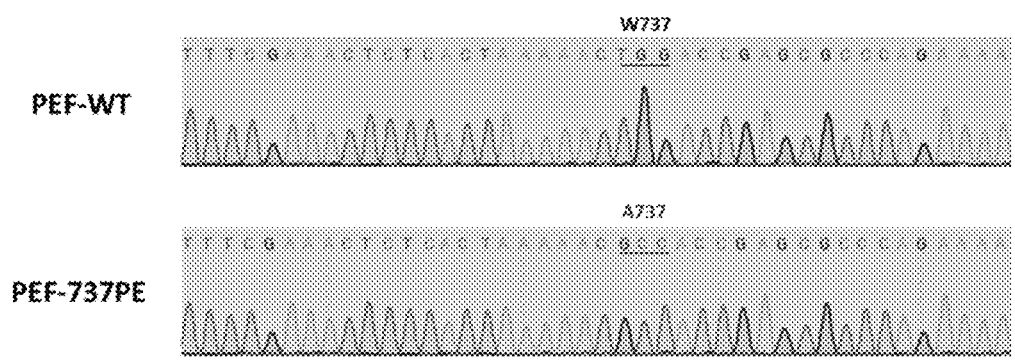
FIG. 11 is a graph of the results of sequencing for porcine fibroblast with precise modification of an amino acid at position 737 in a pAPN protein, as provided in Example 4 of the present invention. The nucleotide sequence of PEF-WT is shown in SEQ ID NO. 20, and the nucleotide sequence of PEF-737PE is shown in SEQ ID NO. 21.

The results of sequencing showed that multiple strains of porcine fibroblasts with precise modification of the amino acid at position 737 in pAPN protein were successfully obtained in this example, and some results of sequencing for the positive cells were shown as FIG. 11.

Example 5. Preparation of a Genetically Edited Pig with Precise Modification of the Amino Acid at Position 737 in pAPN Gene by Somatic Cell Nuclear Transplantation Technology The positive cells obtained from homozygous gene editing in Example 3 were used as donor cells for nuclear transfer, and the enucleated porcine oocytes matured in vitro for 40 h were used as recipient cells for nuclear transfer. The donor cells for nuclear transfer were transferred into the oocytes, which were electrically fused and activated to construct recombinant cloned embryos. The well-developed cloned recombinant embryos were selected and surgically transplanted into the uterus of naturally estrous multiparous white sows for pregnancy. In this process, steps of surgical embryo transfer were as follows: the recipient sow was anesthetized by intravenous injection of Zoletil with a dosage of 5 mg/kg body weight. After anesthesia, the recipient sows were moved to an operating rack for supine fixation, followed by respiratory anesthesia (with a concentration of 3% to 4% isoflurane). An about 10 cm long of surgical incision was made at the midline of the abdomen of the recipient sow to expose ovaries, fallopian tubes, and uterus. An embryo transplantation glass tube was used to enter about 5 cm along the fimbria of the fallopian tubes, and the well-developed cloned recombinant embryos were transplanted to the junction between the ampulla and isthmus of the fallopian tubes. Embryos were regularly observed by the technicians after transplantation, and the pregnancy statuses of the recipient sows were examined by B-type ultrasound. Ear tissues were cut from piglets after birth, followed by extraction of genomic DNA, which was amplified by PCR using pAPN-TY-F2 and pAPN-TY-R2, and the products from PCR amplification were sequenced for genotype detection.

The present invention has been described in detail above. For those skilled in the art, without departing from the purpose and scope of the present invention and without the need for unnecessary experiments, the present invention can be implemented over a wide range of parameters, concentrations, and conditions. Although the present invention provides special Examples, it should be understood that further improvements can be made to the present invention. In summary, according to the principle of the present invention, the present application intends to include any changes, uses, or improvements to the present invention, including changes made outside the disclosed scope of the present application and using conventional techniques known in the art. According to the scope of the accompanying claims, some basic features can be applied.

The invention claimed is:

1. A method for constructing a cell with site-directed modification of a porcine aminopeptidase N (pAPN) gene, which comprises the following steps: introducing a kit comprising a genetically edited protein of Cas9, pAPN-sgRNA-1, pAPN-sgRNA-2, and a donor DNA, wherein the pAPN-sgRNA-1 and pAPN-sgRNA-2 target two different target sequences of the pAPN gene set forth in SEQ ID NO. 1 and SEQ ID NO. 2; and a fragment between the two different target sequences of SEQ ID NO. 1 and SEQ ID NO. 2 is designated as a fragment to be site-directed modified, which comprises a codon encoding tryptophan at position 737 in a pAPN protein; and the donor DNA contains a fragment with site-directed modification, which is obtained by mutating a codon encoding tryptophan at position 737 in the pAPN protein to a codon encoding alanine in the fragment to be site-directed modified or a set of vectors comprising a vector expressing the kit into porcine ileal epithelial cells or porcine fibroblasts to obtain the cell with site-directed modification of the pAPN gene; wherein the donor DNA is double stranded DNA set forth in SEQ ID NO. 3.

2. The method according to claim 1, wherein the set of vectors consists of a vector for expressing the genetically edited protein of Cas9 and the pAPN-sgRNA-1, a vector for expressing the genetically edited protein of Cas9 and the pAPN-sgRNA-2, and a vector containing the donor DNA.

3. The method according to claim 2, wherein the vector for expressing the genetically edited protein of Cas9 and the pAPN-sgRNA-1 is obtained by connecting annealed double stranded DNA fragments from single stranded DNAs set forth in SEQ ID NO. 5 and SEQ ID NO. 6 into a genetically edited backbone vector; alternatively, the vector for expressing the genetically edited protein of Cas9 and the pAPN-sgRNA-2 is obtained by connecting annealed double stranded DNA fragments from single stranded DNAs set forth in SEQ ID NO. 7 and SEQ ID NO. 8 into a genetically edited backbone vector.

* * * * *